United States Patent
Bauer et al.

(10) Patent No.: US 6,395,914 B1
(45) Date of Patent: May 28, 2002

(54) PROCESS FOR PREPARING ACETALS OF MALONDIALDEHYDE

(75) Inventors: Frank Bauer, Bonn (DE); Chitoor Subramaniam, East Brunswick, NJ (US)

(73) Assignee: Creanova, Inc., Piscataway, NJ (US)

( * ) Notice: Subject to any disclaimer, the term of this patent is extended or adjusted under 35 U.S.C. 154(b) by 0 days.

(21) Appl. No.: 09/493,906

(22) Filed: Jan. 28, 2000

(51) Int. Cl.[7] ............................................... C07C 51/00
(52) U.S. Cl. ..................... 554/124; 554/227; 568/603
(58) Field of Search ..................... 554/227; 568/603; 584/124

(56) References Cited

U.S. PATENT DOCUMENTS

| | | | |
|---|---|---|---|
| 2,459,076 A | 1/1949 | Hultquist | 260/615 |
| 2,527,533 A | 10/1950 | Copenhaver | 260/615 |
| 3,373,189 A * | 3/1968 | Lum | 260/497 |
| 4,410,733 A * | 10/1983 | Mangold et al. | 568/603 |
| 4,647,708 A * | 3/1987 | Hunter et al. | 568/883 |
| 4,655,841 A | 4/1987 | Gerhardt | 106/287.23 |

OTHER PUBLICATIONS

Ullmann's Encyclopedia of Industrial Chemistry, 5th Edition, VCH Verlagsgesellschaft, Weinbeim, vol. A1, p. 36–38.

* cited by examiner

Primary Examiner—Deborah D Carr
(74) Attorney, Agent, or Firm—Jay S. Cinamon

(57) ABSTRACT

A process directed to the preparation of acetals of malondialdehyde by reacting alkylvinyl ethers or esters with ortho formates in the gas phase with a heterogeneous catalyst.

18 Claims, No Drawings

PROCESS FOR PREPARING ACETALS OF MALONDIALDEHYDE

FIELD OF THE INVENTION

The present invention relates to a process for preparing acetals of malondialdehyde.

BACKGROUND OF THE INVENTION

Acetals of malondialdehyde of the formula (I):

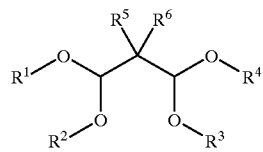

I in which $R^1$, $R^2$, and $R^3$ are the same or different alkyl groups, cycloalkyl groups, aralkyl groups or aryl groups, with up to 12 carbon atoms, $R^4$ is an alkyl group, cycloalkyl group, aralkyl group or represents R—CO— with R=alkyl, cycloalkyl, aralkyl or aryl, and $R^5$ and $R^6$ represent independently of each other H, a cycloalkyl group, an aralkyl group, or an aryl group with up to 12 carbon atoms, are used as intermediates for the preparation of heterocycles such as pyrazols, isoxazols, pyrimidines, 2-aminopyrimidines or pyrimidones. Aside from their use as organic intermediates, they also serve as hardener components for polyvinylalcohol- and polyvinylacetate-films (U.S. Pat. No. 4,655,841).

It is known that the malondialdehyde tetraalkylacetals namely 2-substituted and 2,2-di-substituted malondialdehyde tetraalkylacetals, respectively, can be synthesized by reacting orthoformates with alkylvinyl ethers and substituted alkylvinyl ethers (U.S. Pat. No. 2,527,533) or orthoformates and vinyl esters (U.S. Pat. No. 2,459,076) in the presence of suitable Lewis-acids as the catalyst.

In order to improve the economics of the process, it is desirable to run the reaction in the presence of a heterogeneous catalyst and, optionally, continuously. The use of heterogeneous catalysts for the reaction of orthoformates and vinyl ethers has in fact already been described earlier (U.S. Pat. No. 2,556,321). Also, it has been demonstrated that, for example, methyl vinyl ether and trimethyl orthoformate can be reacted continuously in a tubular reactor using dissolved $FeCl_3$ as the catalyst (EP 0058928).

However, it has been found that the—otherwise advantageous—use of heterogeneous catalysts for the reaction of orthoformates with alkylvinyl ethers leads to several practical problems if conducted conventionally. The most important one is related to catalyst lifetime. Commonly used heterogeneous Lewis acid catalysts, such as acidic montomorillonites and acidic zeolites, as well as otherwise homogeneous Lewis acids, when adsorbed on a suitable support (for example $FeCl_3$ on $SiO_2$) were found to be deactivated after relatively short periods of time. For example, upon the use of montmorillonite K10® or zeolite. H-BEA 25® to catalyze the reaction of methyl vinyl ether with trimethyl orthoformate, the catalyst lost significant activity after only 3 hours. The yields dropped from 80% to <60% and the catalyst slowly darkened. Such short catalyst lifetimes are unacceptable under commercial conditions and, in fact, negate the advantages normally associated with the use of heterogeneous catalysts, i. e. reduced catalyst-costs, reduced disposal costs, and environmental friendliness.

In the cases where otherwise homogeneous Lewis acids like $FeCl_3$, $AlCl_3$ or $ZnCl_2$ were supported on $SiO_2$, $Al_2O_3$ or montmorillonites or the commercially available Envirocats® were used, the catalysts quickly lost their activity, and the products were found to contain significant amounts of the catalyst-cations. This phenomenon is commonly referred to as 'leaching'.

It is accordingly an object of the present invention to provide a process that provides the compounds of general formula I from orthoformates and alkylvinyl ethers or orthoformates and vinyl esters in the presence of heterogeneous catalysts without the drawback of unacceptably short catalyst lifetimes.

SUMMARY OF THE INVENTION

It is an object of the present invention to provide a process for preparing acetals of malondialdehyde of general formula I:

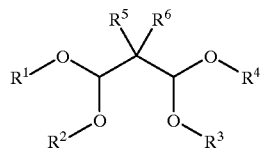

I in which $R^1$, $R^2$, and $R^3$ are the same or different alkyl groups, cycloalkyl groups, aralkyl groups or aryl groups with up to 12 carbon atoms, $R^4$ is an alkyl group, cycloalkyl group, aralkyl group; aryl group, or represents $R^7$—CO— with $R^7$=alkyl, cycloalkyl, aralkyl, or aryl with up to 12 carbons, and $R^5$ and $R^6$ represent independently of each other H, an alkyl group, cycloalkyl group, aralkyl group or an aryl group with up to 12 carbon atoms, by reacting alkylvinyl ethers of general formula II or vinyl esters of general formula III:

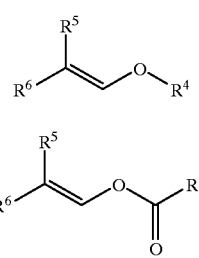

II

III and ortho formates of general formula IV:

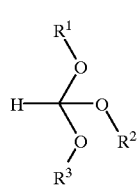

IV wherein the reaction is carried out in the gas phase using a catalyst.

DETAILED DESCRIPTION OF THE INVENTION

The present invention provides a process for preparing acetals of malondialdehyde of general formula I:

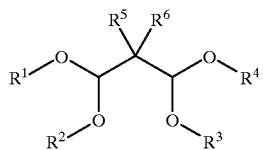

I in which $R^1$, $R^2$, and $R^3$ are the same or different alkyl groups, cycloalkyl groups, aralkyl groups, or aryl groups with up to 12 carbon atoms, $R^4$ is an alkyl group, cycloalkyl group, aralkyl group, aryl groups, or represents $R^7$—CO— with $R^7$=alkyl, cycloalkyl, aralkyl, aryl with up to 12 carbon atoms, and $R^5$ and $R^6$ represent independently of each other H, an alkyl group, cycloalkyl group, arylalkyl group, or aryl group, with up to 12 carbon atoms which allows for the use of a heterogeneous catalyst under commercial conditions and which leads to superior selectivities.

In a preferred embodiment of the process according to the present invention, $R^1$, $R^2$ and $R^3$ are identical. It is especially preferred that in the compound of formula I, $R^1$, $R^2$, $R^3$ and $R^4$ represent a methyl group. It is also especially preferred that in the compound of general formulas I, $R^1$, $R^2$ and $R^3$ represent a methyl group and $R^4$ represent an acetyl group.

It has been found that improved catalyst-lifetimes of heterogeneous catalysts, as well as superior selectivities, can be achieved in a simple manner and that acetals of malondialdehyde of general formula I are obtained advantageously if alkyl vinylethers of general formula II or a vinylester of general formula III:

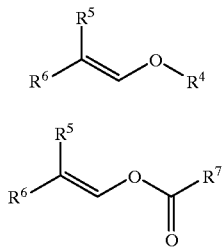

II

III in which $R^4$, $R^5$ and $R^6$ are as defined above and $R^7$ is an alkyl group, cycloalkyl group, aralkyl group, or aryl group, with up to 12 carbon atoms, are reacted with an orthoformate of general formula IV

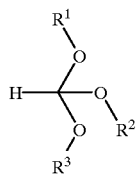

IV in the gas phase.

Acidic catalysts, preferably strong Lewis acids, such as $ZnCl_2$ on montmorillonite K-306®, $ZnCl_2$ on $Al_2O_3$, $FeCl_3$ on $SiO_2$ or Envirocats EPZG® and EPZ10® demonstrated relatively high reactivities and, therefore, are preferred.

In order to evaporate the starting materials and especially to avoid condensation of the products of general formula I and/or the starting materials of general formula II respective III and IV within the catalyst bed, it has been found to be advantageous to carry out the reaction under vacuum. In a preferred embodiment according to the present invention, the reaction is carried out at an absolute pressure between about 0.1 mm Hg and about 500 mm Hg, with a pressure of between about 1 mm Hg, and about 50 mm Hg being especially preferred.

While the compounds of general formula II respective III and IV can be reacted in the gas phase at temperatures as low as 20° C., it is advantageous to choose temperatures that are significantly higher than the ones that are ideal for the liquid phase. Above 250° C., however, the orthoformates of general formula IV were found to decompose to a significant extent, even on very short contact-times. The best yields of the compounds of general formula I were usually achieved in the temperature range of about 40° C. to about 150° C., and especially in the temperature range of about 70° C. to about 100° C.

Improved conversions of the starting materials of general formulas II and III are usually achieved if the ortho formates of general formula IV are used in excess, i.e., from about 1.1 to about 3-fold molar excess, preferably about 1.2-fold to about 1.5 fold.

In a preferred embodiment of the process according to the present invention, the reaction is carried out continuously. In practice, it does not matter if a mixture of the compounds of formulas II, III and IV are evaporated, or if individual vapor streams are passed through a common catalyst bed.

It is a special advantage of the process according to the present invention that the separation of the products of general formula I from the starting materials of general formulas II, III and IV can be easily achieved by fractional condensation. In a preferred embodiment, the product of general formula I, unconverted starting materials of general formulas II, III and IV, or a mixture thereof, as well as lower boiling byproducts, such as dialkyl ethers or alkyl formates, are condensed separately by adjustment of the condensation temperatures.

If necessary, the product of general formula I, as well as the recovered starting materials of general formulas II, III and/or IV can then be further purified by standard techniques, preferably by fractional distillation.

In a preferred embodiment according to the present, invention, the recovered starting materials of general formulas II, III and/or IV are recycled back into the process. In doing so, it has been found that a removal of protic contaminants, such as alkanols, is advantageous with respect to obtaining improved yields.

Having described the present invention, reference will now be made to certain examples, which are provided solely for purposes of illustration and are not intended to be limiting.

EXAMPLE 1

1,1,3,3-Tetramethoxypropane

A mixture of 20.61 g (0.36 mole) of methylvinyl ether and 48.99 g (0.46 mole) of trimethyl orthoformate was continuously evaporated into a vacuum-line (50 mbar) within 1.0 hours. The gas mixture was passed over a heated (84° C.) fixed-bed catalyst (length of catalyst-bed: 9 cm; diameter of catalyst-bed: 1.5 cm). By condensation at −78° C., 65.11 g product-mixture were received. A gas chromatographic analysis indicated the formation of 1,1,3,3-tetramethoxypropane (1.4 FID-area-%).

The heterogeneous catalyst was prepared by doping 100.00 g $Al_2O_3$ beads with 5.0 g $ZnCl_2$. 1000 g of acetonitrile were used as the solvent.

EXAMPLE 2

1,1,3,3-Tetramethoxypropane

The experimental procedure of Example 1 was followed except that the below catalyst was used. Analysis of the condensate (65.40 g) revealed the formation of 1,1,3,3-tetramethoxy propane (4.0 FID-area-%).

The heterogeneous catalyst was prepared by doping montmorillonite K-306 beads with 3.0 g $PdCl_2(ACN)_2$, 5.0 g $ZnCl_2$, and 1.0 g $CuCl_2$. 1000 g of acetonitrile were used as the solvent. Before its use, the catalyst was conditioned with 1.0 g $BF_3{}^*OEt_2$ and 25.0 g trimethyl ortho formate and subsequently dried for 3.0 hours at 80° C./oil pump vacuum in order to remove the excess of reagents.

EXAMPLE 3

1,1,3,3-Tetraethoxypropane

A mixture of 20.00 g (0.28 mole) of ethylvinyl ether and 41.11 g (0.28 mole) of triethyl orthoformate was continuously evaporated into a vacuum-line (45 mbar) within 1.0 hours. The gas mixture was passed over a heated (90° C.) fixed-bed catalyst (length of catalyst-bed: 9 cm; diameter of catalyst-bed: 1.5 cm). By condensation at −78° C., 59.48 g product-mixture were received. A gas chromatographic analysis indicated the formation of 1,1,3,3-tetraethoxypropane (5.8 FID-area-%).

The heterogeneous catalyst of Example 2 was re-used.

EXAMPLE 4

2-Ethyl-1,1,3,3-tetramethoxypropane

A mixture of 25.01 g (0.29 mole) of ethyl-1-propenyl ether and 40.06 g (0.38 mole) of trimethyl orthoformate was continuously evaporated into a vacuum-line (40 mbar) within 1.0 hours. The gas mixture was passed over a heated (85° C.) fixed-bed catalyst (length of catalyst-bed: 9 cm; diameter of catalyst-bed: 1.5 cm). By condensation at −78° C., 63.76 g product-mixture were received. A gas chromatographic analysis indicated the formation of 2-methyl-1-ethoxy-1,3,3-trimethoxy-propanes (2.5 FID-area-%). The heterogeneous catalyst of Example 3 was re-used.

EXAMPLE 5

1,1,3,3-Tetramethoxypropane and 1,1,3-Trimethoxy-3-acetoxypropane

A mixture of 50.0 g (0.58 mole) of vinylacetate and 53.0 g (0.50 mole) of trimethyl orthoformate was continuously evaporated into a vacuum-line (30 mbar) within 1.0 hours. The gas mixture was passed over a heated (80° C.) fixed-bed catalyst (length of catalyst-bed: 10 cm; diameter of catalyst-bed: 2 cm). By condensation at −78° C., 101.9 g product-mixture were received. A gas chromatographic analysis showed the formation of 1,3,3-trimethoxy-1-acetoxypropane and 1,1,3,3-tetramethoxy-propane in a ratio of 1:1. By quantification of the non-converted trimethyl orthoformate as well as the products, the trimethyl orthoformate-losses due to fragmentation and other side reactions were calculated to be only 2.0%.

The heterogeneous catalyst was prepared by doping montmorillonite K-306 beads with 3.0 g $PdCl_2(ACN)_2$, 5.0 g $ZnCl_2$, and 1.0 g $CuCl_2$. 1000 g of acetonitrile were used as the solvent. Before its use, the catalyst was conditioned with 1.0 g $BF_3{}^*OEt2$ and 25.0 g trimethyl ortho formate and subsequently dried for 3.0 hours at 80° C./oil pump vacuum in order to remove the excess of reagents.

What is claimed is:

1. A process for preparing acetals of malondialdehyde of general formula I:

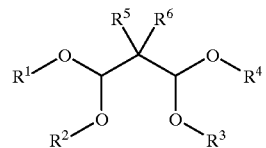

I in which $R^1$, $R^2$, and $R^3$ are the same or different alkyl groups, cycloalkyl groups, aralkyl groups, or aryl groups with up to 12 carbon atoms, $R^4$ is an alkyl group, cycloalkyl group, aralkyl group, or represents $R^7$—CO— with $R^7$=alkyl, cycloalkyl, aralkyl, or aryl, with up to 12 carbon atoms, and $R^5$ and $R^6$ represent independently of each other H, an alkyl group, a cycloalkyl group, an aralkyl group or an aryl group with up to 12 carbon atoms, which process comprises reacting an alkyl vinylether of general formula II or a vinylester of general formula III:

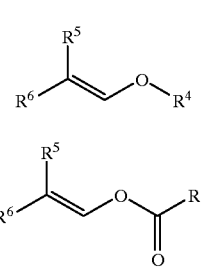

II

III in which $R^4$, $R^5$ and $R^6$ are as defined above and $R^7$ is an alkyl group, cycloalkyl group, aralkyl group, or aryl group with up to 12 carbon atoms, with an ortho formate of general formula IV:

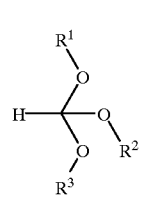

IV in the gas phase using an acidic heterogeneous catalyst under a vacuum of from about 0.5 mm to about 500 mm Hg.

2. The process of claim 1, wherein the catalyst is a Lewis-acid catalyst.

3. The process of claim 1, wherein the catalyst comprises a Friedel-Crafts catalyst.

4. The process of claim 1, wherein the catalyst comprises a precious metal compound selected from the group consisting of compounds of Ru, Rh, Pd, Os, Ir and Pt.

5. The process of claim 1, wherein the reaction is carried out under a vacuum from about 1 mm to about 50 mm Hg.

6. The process of claim 1, wherein the reaction is conducted in the range of about 20° C. to about 250° C.

7. The process of claim 6, wherein the reaction is conducted in the range of about 40° C. to about 150° C.

8. The process of claim 7, wherein the reaction is conducted in the range of about 70° C. to about 100° C.

9. The process of claim 4, wherein the catalyst contains at least one compound capable of catalyzing the oxidation of the precious metals to oxidation states >0.

10. The process of claim 9, wherein the catalyst is selected from the group consisting of $CuCl_2$, $FeCl_3$, or mixtures thereof.

11. The process of claim 4, wherein the reaction is carried out in the presence of an oxidant.

12. The process of claim 1, wherein the reaction is carried out in the presence of an oxidant.

13. The process of claim 1, wherein about a 1.1-fold to about a 3-fold molar excess of the orthoformate of general formula IV is employed compared to the vinylether of general formula II or the vinylester of general formula III.

14. The process of claim 13, wherein about a 1.2 fold to 1.5 fold molar excess of the orthoformate of general formula IV is employed compared to the vinylether of general formula II or the vinylester of general formula III.

15. The process of claim 1, wherein the reaction is carried out continuously.

16. The process of claim 1, wherein the compounds of general formula I and the unconverted starting materials of general formulas II and III are separated by fractional condensation.

17. The process of claim 1, wherein the products and the unconverted starting materials, or both, are further purified by distillation.

18. The process of claim 1, wherein unconverted starting materials are recycled back into the process.

* * * * *